(12) United States Patent
Miwa

(10) Patent No.: US 6,602,192 B2
(45) Date of Patent: Aug. 5, 2003

(54) NONCONTACT TYPE TONOMETER

(75) Inventor: Tetsuyuki Miwa, Nukata-gun (JP)

(73) Assignee: Nidek Co., Ltd. (JP)

( * ) Notice: Subject to any disclaimer, the term of this patent is extended or adjusted under 35 U.S.C. 154(b) by 0 days.

(21) Appl. No.: 09/813,171

(22) Filed: Mar. 20, 2001

(65) Prior Publication Data

US 2001/0009973 A1 Jul. 26, 2001

Related U.S. Application Data

(60) Division of application No. 08/351,583, filed on Dec. 7, 1994, now Pat. No. 6,234,966, which is a continuation-in-part of application No. 07/933,303, filed on Aug. 21, 1992, now abandoned.

(30) Foreign Application Priority Data

Aug. 31, 1991 (JP) .............................. 3-246643

(51) Int. Cl.$^7$ ................................ A61B 5/05
(52) U.S. Cl. .................................... 600/401
(58) Field of Search .............................. 600/401, 405, 600/398, 406

(56) References Cited

U.S. PATENT DOCUMENTS

| 3,585,849 A | 6/1971 | Grolman | 73/80 |
|---|---|---|---|
| 4,344,037 A | 8/1982 | Ragsdale | 328/114 |
| 4,817,620 A * | 4/1989 | Katsuragi et al. | 600/401 |
| 4,947,849 A | 8/1990 | Takahashi et al. | 128/648 |
| 5,031,623 A | 7/1991 | Kohayakawa et al. | 128/648 |
| 5,042,484 A | 8/1991 | Hideshima | 128/648 |
| 5,092,334 A * | 3/1992 | Nishio et al. | 600/401 |
| 5,107,851 A | 4/1992 | Yano et al. | 128/648 |
| 5,183,044 A * | 2/1993 | Nishio et al. | 600/398 |
| 5,190,042 A * | 3/1993 | Hock | 600/405 |
| 5,279,300 A | 1/1994 | Miwa et al. | 128/648 |
| 6,234,966 B1 * | 5/2001 | Miwa | 600/401 |

FOREIGN PATENT DOCUMENTS

JP 63-300740 A 12/1988

* cited by examiner

Primary Examiner—Max F. Hindenburg
Assistant Examiner—Brian Szmal
(74) Attorney, Agent, or Firm—Rossi & Associates

(57) ABSTRACT

A noncontact type tonometer monitors the rate of change X(t) in pressure between a standard curve and a measured curve. If X(t) exceeds a value of 1.3, the application of air pressure is stopped to prevent an abnormal rise in pressure. If X(t) is equal to 1, then the measured curve follows the standard curve and correction is not required. If X(t) is not equal to 1, an error condition exists and an amended time t' is calculated based on the rate of change X(t). Instead of a calculated amended time, an approximated standard curve can also be determined based on either an equation stored in a memory or by matching the measured curve with one of a plurality of standard curves stored in memory.

11 Claims, 4 Drawing Sheets

NONCONTACT TYPE TONOMETER

CROSS-REFERENCE TO RELATED APPLICATIONS

The present invention is a division of Ser. No. 08/351,583, filed Dec. 7, 1994 now U.S. Pat. No. 6,234,966, which is a cip application of, and claims priority from, U.S. patent application Ser. No. 07/933,303, filed Aug. 21, 1992, now abandoned, the contents of which are herein incorporated.

FIELD OF THE INVENTION

The present invention relates to a noncontact tonometer by which intraocular pressure of a patient's eye is measured, without contacting the eye, by directing a compressed air pulse into a cornea of the patient's eye and deforming the cornea in a predetermined manner. More particularly, the present invention relates to a noncontact type tonometer in which intraocular pressure of the patient's eye can be precisely measured without being affected by atmospheric changes or giving discomfort to the patient.

BACKGROUND

A noncontact type tonometer, in which intraocular pressure of the patient's eye is measured by directing compressed air to the cornea of the patient's eye and applanating thereof, is well-known. U.S. Pat. No. 3,585,849, for example, discloses a noncontact tonometer in which the intraocular pressure of the patient's eye is measured based on an elapsed time interval during which a surface of the cornea deforms into a flat state from a convex state while being deformed by a compressed air pulse directed thereto. In the noncontact type tonometer mentioned above, the pressure of the air pulse necessary to deform the cornea to the flat state is indirectly obtained according to the time interval elapsed during which the surface of the cornea deforms into the flat state from the convex state, assuming that the pressure of the air pulse is controlled correctly based on the optimum control condition.

Additionally, in Japanese Patent Application after substantive examination, Laid-open No. SHO 63-58577, a noncontact type tonometer in which, the pressure of the air pulse corresponding to the flat state of the cornea is directly obtained from a pressure sensor arranged in a device for producing the air pulse.

However, in the former tonometer, measuring accuracy thereof depends on whether or not the air pulse producing device is controlled under the predetermined optimum control condition. Therefore, the measuring accuracy of the air pulse pressure in the tonometer will not be reliable unless the air pulse producing device is controlled under the predetermined optimum control condition.

The determining method of the air pulse pressure according to the above tonometer will be described based on FIG. 5. FIG. 5 is a graph to explain the determining method of the air pulse pressure in the conventional tonometer, in which the ordinate shows the air pulse pressure, the abscissa shows time, f is a standard curvature which shows change of the air pulse pressure versus time (abbreviated "standard p-t curvature" hereinafter), g is an actually measured curvature with various error which shows change of the air pulse pressure versus time (abbreviated "actual p-t curvature" hereinafter), h is a curvature which shows change of light quantity reflected from the cornea and maximum light quantity is obtained at a time t because the cornea deforms to the flat state at the time t, p(t) is the air pulse pressure obtained from the standard p-t curvature f at the time t, t' is a time at which the maximum light quantity will be obtained if the air pulse pressure is measured without any error and p'(t) is the air pulse pressure obtained from the standard p-t curvature f at the time t'.

According to FIG. 5, the air pulse pressure is measured based on a condition (such condition is deviated from the predetermined optimum condition) including various errors such as atmospheric change surrounding the tonometer, mechanical error produced in a piston mechanisms of the air pulse producing device, the air pulse pressure is determined as p(t) at the time t according to the standard p-t curvature f in FIG. 5, since the air pulse pressure is obtained based on the time t at which the maximum light quantity reflected from the cornea is detected because of the flat state thereof. Thereafter, the intraocular pressure of the patient's eye is calculated from the air pulse pressure p(t). Such obtained air pulse pressure p(t) deviates from the air pulse pressure p'(t) to be obtained without any error at the time t'. As mentioned above, a defect in the measuring error of the air pulse pressure will be caused by the above various errors which exist in the conventional tonometer.

In the latter tonometer, the measuring error of the air pulse pressure is not caused by the atmospheric change or the mechanical error mentioned above, and reproducibility in measuring of the air pulse pressure is good because the intraocular pressure of the patient's eye is calculated based on the air pulse pressure directly detected by the pressure sensor at the time when the maximum light quantity reflected from the cornea is obtained. However, in the latter tonometer, after the air pulse pressure is produced, the change of the air pulse pressure versus time is not monitored, therefore, early detection of the abnormal state in the air pulse pressure caused by a malfunction of the piston in the air pulse pressure producing device or binding in a nozzle part formed in the air pulse pressure producing device to direct the compressed air pulse to the cornea of the patient's eye cannot be conducted. Further, excessive air pulse pressure may be directed to the cornea of the patient's eye, giving discomfort to the patient, since the change in the air pulse pressure versus time is not monitored in the latter tonometer.

SUMMARY OF THE INVENTION

Accordingly, it is an object of the present invention to overcome the above-mentioned problems and to provide a noncontact type tonometer in which the air pulse pressure can be correctly measured without being affected by various errors such as the atmospheric change and the mechanical error caused in the piston mechanism in the air pulse pressure producing device and the application of excessive air pulse pressure to the cornea of the patient's eye can be avoided.

To accomplish the above object, the present invention comprises a noncontact type tonometer having a compressing means for forming compressed air, a direction means for directing the compressed air to a cornea of a patient's eye and a deformation detection means for detecting deformation state of the cornea to which the compressed air is directed by the direction means, the noncontact type tonometer further comprising: a memory means for storing a standard pressure characteristic of the compressed air which changes according to passage of time, a pressure detection means for detecting pressure change of the compressed air directed by the direction means, a time detection means for detecting the time elapsed until the deformation detection means detects a flat state of the cornea, a comparison means for comparing the pressure change of the compressed air detected by the pressure detection means with the standard pressure characteristic stored in the memory means, an amendment means for amending the time detected by the time detection means according to the standard pressure characteristic based on result compared by the comparison means, and a first calculation means for calculating an intraocular pressure of the patient's eye based on the amended time by the amendment means.

In the present invention, the compressed air is directed to the cornea of the patient's eye by the direction means. During direction of the compressed air, the shape of the cornea is deformed from the convex state to the flat state, and while the cornea is deforming, the deformation state of the cornea is detected by the deformation detection means and the pressure change of the compressed air is detected by the pressure detection means, and further, the time elapsed until the deformation detection means detects the flat state of the cornea is detected by the time detection means.

Next, the comparison means compares the pressure change detected by the pressure detection means with the standard pressure characteristic stored in the memory means. Following this comparison by the comparison means, the time detected by the time detection means is amended according to the standard pressure characteristic based on the compared result. Thereafter, the intraocular pressure of the patient's eye is calculated based on the amended time by the first calculation means.

Therefore, according to the present invention, fluctuation of the intraocular pressure can be prevented, thus, the precise intraocular pressure can be stably obtained, because delicate change in the measured air pressure caused due to the atmospheric change or the mechanical error can be eliminated.

Further, abnormal rises in the air pressure can be prevented, thus, discomfort will not be given to the patient, because the air pressure changing state is continuously monitored.

BRIEF DESCRIPTION OF THE DRAWINGS

The invention will be described in greater detail with reference to the following drawings, wherein.

DETAILED DESCRIPTION OF THE PREFERRED EMBODIMENTS

A detailed description of the preferred embodiment of a noncontact type tonometer embodying the present invention will now be given referring to the accompanying drawings.

Figure 1:
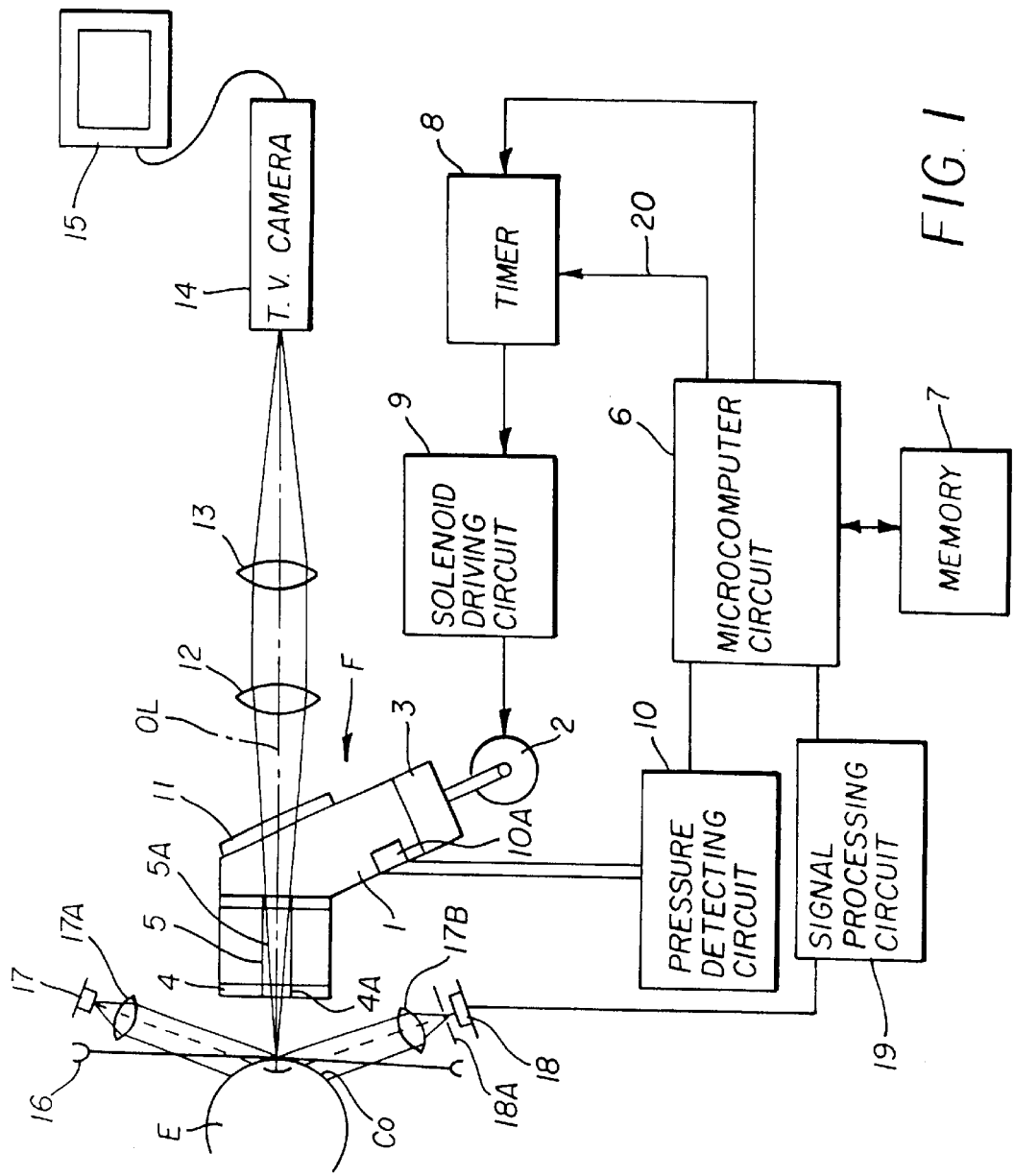
FIG. 1 is a block diagram of a tonometer in accordance with a preferred embodiment of the present invention.

Referring to FIG. 1, a device F for directing compressed air to a cornea CO of a patient's eye E is constructed from a cylinder 1 and a piston 3 slidably arranged in the cylinder 1 and further connected to a rotary solenoid 2. To the left-hand part (in reference to the drawing) of the cylinder 1 in FIG. 1, a nozzle 5, in which a nozzle hole 5A is formed, is attached. A window plate 4, in which a window part 4A is formed, is attached in front of the nozzle 5. The window plate 4 is arranged toward the cornea CO of the patient's eye E. In the window plate 4, the window part 4A, corresponding to the optical path of luminous flux for positioning thereof, is made of clear glass.

Accordingly, air, which is compressed in the cylinder 1 by the piston 3 that is activated by the driven rotary solenoid 2, is directed to the cornea CO of the patient's eye E through both the nozzle hole 5A of the nozzle 5 and the window part 4A of the window plate 4. It will be readily understood by those skilled in the art that a linear motor having a reaction rail and a slider may also be used in this tonometer instead of the rotary solenoid 2.

A control system for the air directing device F mentioned above will be described hereinafter. Control of the air directing device F is conducted by a microcomputer circuit 6 having CPU, ROM and RAM. The CPU calculates various data based on the control program (later mentioned) stored in the ROM. The CPU then temporarily stores the calculated results in the RAM. Further, a memory 7 is connected to the microcomputer circuit 6 for storing various data measured and measuring condition at that time.

A timer 8 is connected to the microcomputer circuit 6. A solenoid driving circuit 9 is connected between the timer 8 and the rotary solenoid 2. Thus, when the rotary solenoid 2 is driven, the microcomputer circuit 6 sets the solenoid driving time to the timer 8 through a line 20, thereby, the solenoid driving circuit 9 drives the rotary solenoid 2 during the solenoid driving time set to the timer 8.

For controlling the solenoid driving time, a condenser charging control circuit can be applied. A condenser is installed in the condenser charging control circuit and the charging time of the condenser is variably changed according to the solenoid driving time set to the timer 8. Thereby, the solenoid driving time is controlled by electric energy applied to the rotary solenoid 2.

The solenoid driving time can be controlled by a control circuit for controlling a voltage applying time. In such the control circuit, the voltage applying time to the rotary solenoid 2 is variably changed by a switching circuit installed therein. Thereby, the solenoid driving time is controlled.

Further, the solenoid driving time may be controlled by a control circuit for controlling the applying time of an electric current. In such the control circuit, the applying time of an electric current to the rotary solenoid 2 is variably changed by a switching circuit installed therein. Thereby, the solenoid driving time is controlled.

A pressure detecting circuit 10 is connected to the cylinder 1, and this pressure detecting circuit 10 has a pressure sensor 10A which continuously detects the pressure of the compressed air in the cylinder 1 according to the compression of the air by the piston 3. The pressure detecting circuit 10 outputs the detected pressure data to the microcomputer circuit 6. Here, the pressure sensor 10A can be arranged anywhere in a nozzle extending from the cylinder 1, though it is arranged in the cylinder 1 in this embodiment.

Next, the optical system of the tonometer will be described. The optical axis OL passing through center of the cornea CO coincides with the screening optical path in order to screen a front image of the patient's eye E. At a part of the cylinder 1, through which the screening optical path passes, a clear glass plate 11 is arranged. An objective lens 12, an imaging lens 13 and T.V. camera 14 sensitive to the light in the near infrared range are aligned on the optical axis OL.

A half mirror (not shown but well-known in the art) is arranged between the clear glass plate 11 and the T.V. camera 14. Thus, according to this half mirror, the optical axis of the screening optical path forming the Purkinje image is made coaxial with the optical axis OL. A T.V. monitor 15 is connected to the T.V. camera 14 and, on the T.V. monitor 15, the front image of the patient's eye E, taken by the T.V. camera 14, and the measured result of the intraocular pressure are displayed.

Numeral 16 designates a light source for irradiating the front part of the patient's eye E. Numeral 17 is a measuring light source which radiates near infrared light to the cornea CO for measuring the flat state of the cornea CO. The light emitted from the measuring light source 17 passes through a collimating lens 17A and becomes a parallel luminous flux. Thereafter, the luminous flux, as a measuring light, is directed to the cornea CO. The measuring light that is reflected from the cornea CO is condensed by a condenser lens 17B and is directed to a photo detector 18 after passing through a pin hole 18A. Here, the photo detector 18 is arranged to such a position where a maximum light quantity can be obtained from the cornea CO when the cornea CO is applanated to a flat state. The photo detector 18 continuously detects incident light, and the optical data signal detected by the photo detector 18 is transmitted to the microcomputer circuit 6 through a signal processing circuit 19.

Here, a construction disclosed in the Japanese application laid-open No. 63-300740, in which a half mirror is arranged so as to become coaxial with an optical path, can be used in the tonometer of the present invention, though various relations about the arranging position between the measuring light source 17 and the photo detector 18 and detecting method of the flat state of the cornea CO are proposed.

Figure 2:
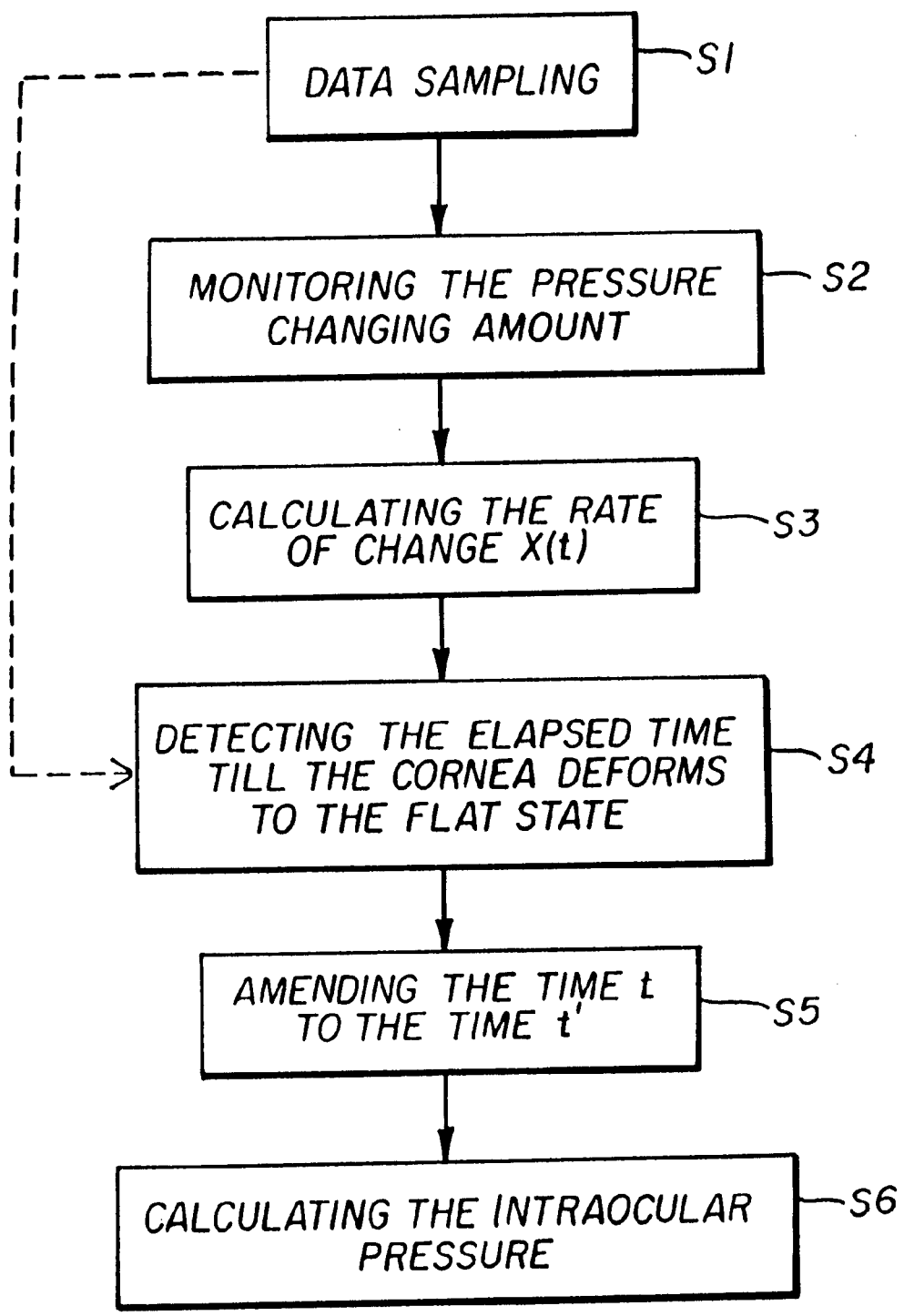
FIG. 2 is a flow chart of control program conducted by the control system.

Operation of the above constructed tonometer will be described hereinafter according to FIGS. 2, 3, and 4. First, both the front part of the patient's eye E and the tonometer are mutually aligned so that the patient's eye E and the tonometer have a predetermined relationship, while observing the front part of the patient's eye E through the T.V. monitor 15. When the observer depresses a start switch of the tonometer to start measurement, the microcomputer circuit 6 outputs a start signal to the timer 8 through the line 20, thereby the rotary solenoid 2 is driven by the solenoid driving circuit 9 during the solenoid driving time set to the timer 8. Thus, the piston 3 compresses the air in the cylinder 1 and the compressed air is directed to the cornea CO of the patient's eye E through the nozzle 5. The cornea CO gradually deforms its shape from the convex state to the flat state by the compressed air and when the cornea CO reaches to the flat state, the reflected light quantity on the cornea CO in the flat state reaches to the maximum quantity and such maximum light quantity is input to the photo detector 18.

The signals detected by the pressure sensor 10A and the photo detector 18 are serially processed in the pressure detecting circuit 10 and the signal processing circuit 19, thereafter input to the microcomputer circuit 6 in step (abbreviated "S" hereinafter) 1.

Here, the change in the pressure data processed by the pressure detecting circuit 10 versus the passing time is detected with the time by the microcomputer circuit 6. Further, the pressure changing amount according to the passing time is continuously monitoring by the microcomputer circuit 6 as the gradient a'(t) of the actual p-t curvature G (shown in FIG. 3) at the time t (S2). The gradient a'(t) is defined by the equation: a'(t)=p'(t)/t. And the gradient a(t) of the standard p-t curvature F (shown in FIG. 3) at the time t is defined by the equation: a(t)=p(t)/t.

Figure 3:
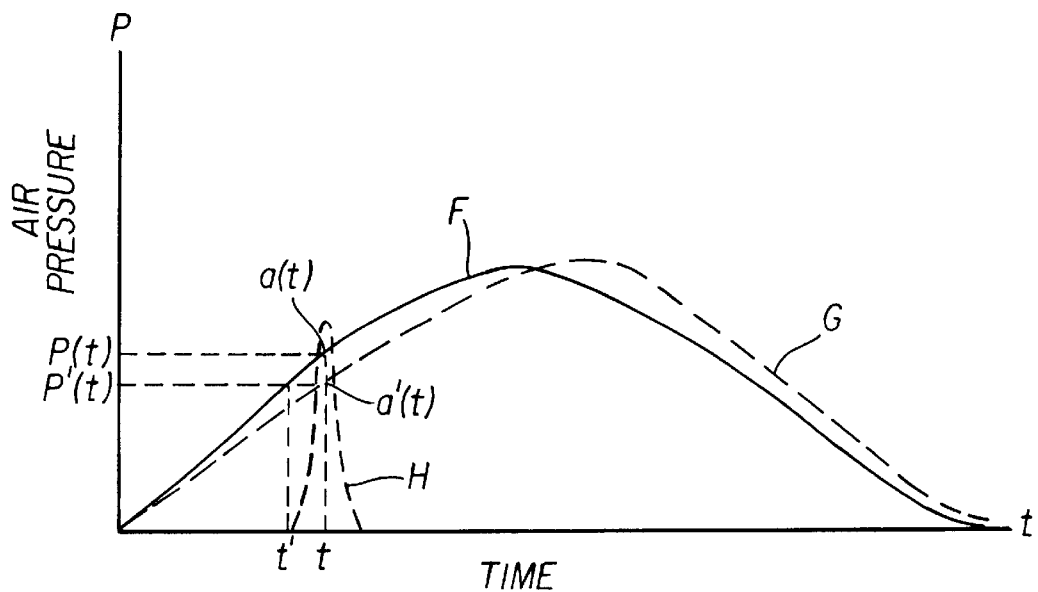
FIG. 3 is a graph to explain the determining method of the air pulse pressure in the preferred embodiment of the present invention.
Figure 5:
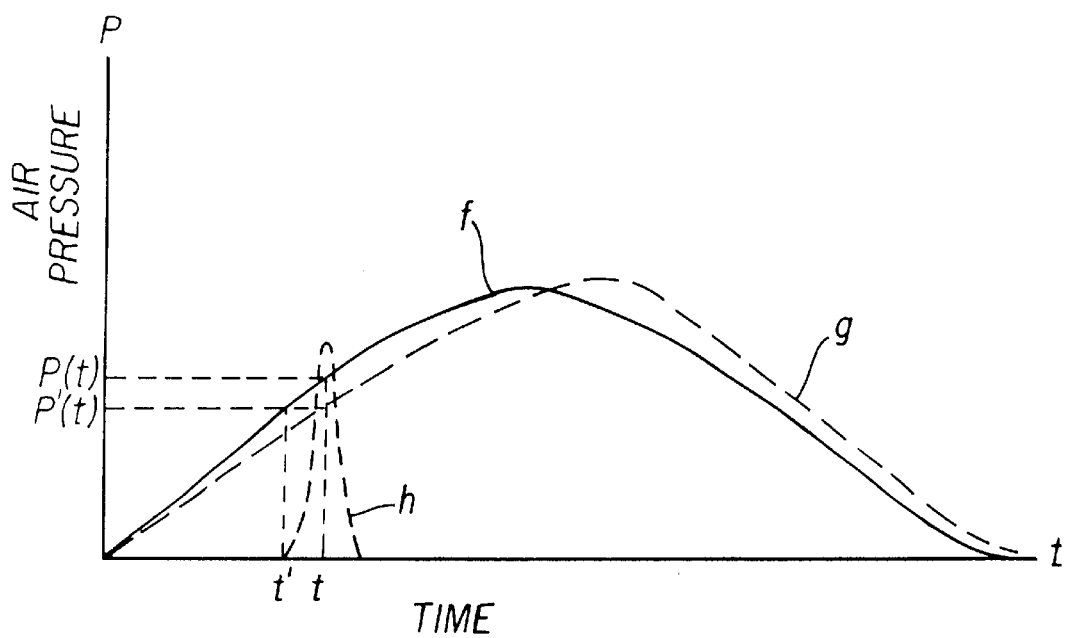
FIG. 5 is a graph to explain the determining method of the air pulse pressure in the conventional tonometer.

FIG. 3 is a same graph as the graph shown in FIG. 5, to explain the determining method of the air pulse pressure in the tonometer, in which the ordinate shows the air pulse pressure, the abscissa shows time, F is a standard curvature which shows change of the air pulse pressure versus time, G is an actually measured curvature with various error which shows change of the air pulse pressure versus time, H is a curvature which shows change of light quantity reflected from the cornea and the maximum light quantity is obtained at a time t because the cornea deforms to the flat state at the time t, p(t) is the air pulse pressure obtained from the standard p-t curvature F at the time t, t' is a time at which the maximum light quantity will be obtained if the air pulse pressure is measured without any error and p'(t) is the air pulse pressure obtained from the standard p-t curvature F at the time t'.

And further in S3, the rate of change X(t) in the pressure versus the passing time, which is defined by the equation: X(t)=a'(t)/a(t), is calculated by the microcomputer circuit 6. The microcomputer circuit 6 compares the calculated rate of change X(t) with the predetermined value and if it is judged by the microcomputer circuit 6 that the calculated rate of change X(t) exceeds the predetermined value, a stop signal is input to the solenoid driving circuit 9 from the microcomputer circuit 6. As a result, driving-of the rotary solenoid 2 is stopped immediately, thereby it can be prevented the air pressure from rising abnormally. Here, the predetermined value of the rate of change X(t) is set to the value 1.3.

Here, if the rate of change X(t) is equal to 1 (that is the gradient a'(t)=the gradient a(t)) in case that the rate of change X(t) does not exceed the predetermined value, the time t is equal to the time t' because the actual p-t curvature G mutually coincides with the standard p-t curvature F, therefore it is not necessary to amend the time t to the time t'. On the other hand, if the rate of change X(t) is not equal to 1 (in this case, the atmospheric change or the mechanical error exists), the time t is amended based on the rate of change X(t) as mentioned hereinafter.

Figure 4:
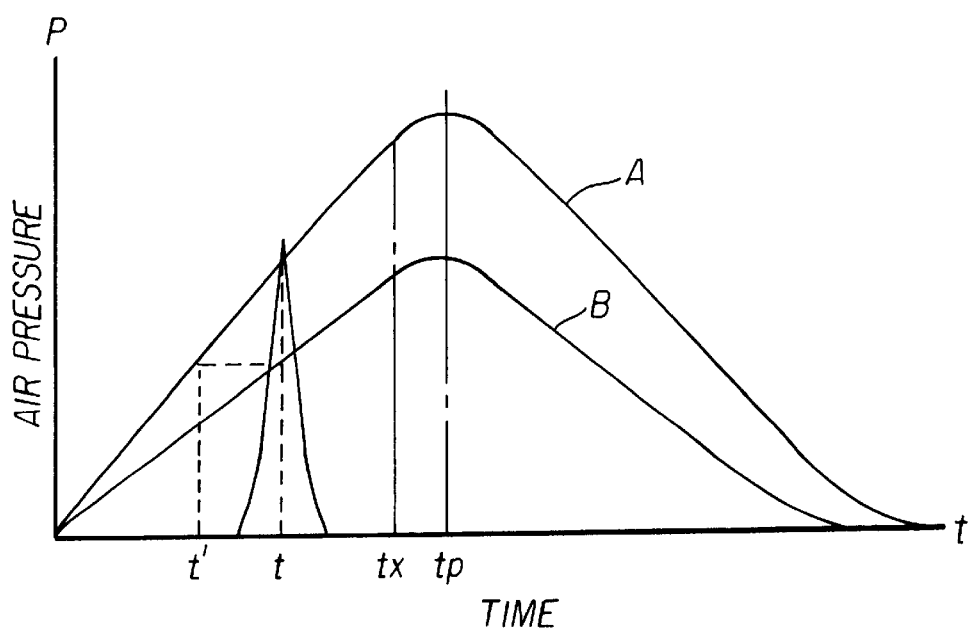
FIG. 4 is a graph to explain amending method of the actually measured time t at which the maximum light quantity reflected from the cornea is obtained, to the time t' based on rate of change in the air pulse pressure calculated by using both the standard p-t curvature and the actual p-t curvature.

Generally speaking, in case that the compressed air is directed to the cornea CO in the tonometer, the air pressure directed to the cornea CO is linearly changed until the predetermined time tx has elapsed as shown in the curvatures A and B in FIG. 4. Here, the time tx means a time point where the gradients a'(t), a(t) shown in FIG. 3 changes from the constant value, that is, the straight line converts to the curved line, and the time tx fluctuates according to driving state of the rotary solenoid 2 or the mechanical error.

Assuming that the curvature A is the standard p-t curvature utilized for calculating the intraocular pressure, the actually measured air pressure which changes according to the curvature B may include the error represented by the rate of change X(t) against the air pressure which changes according to the curvature A, if the air pressure of the curvature B changes linearly until the time tx. Therefore, it is necessary to amend the time t which is actually measured in order to eliminate such error. Thus, the time t is amended based on the rate of change X(t) at the time tx, as a result, the amended time t' defined by the equation: t'=t·X(tx) can be obtained (S4, S5).

Here, complex operation of the control program will be unnecessary because the rate of change X(tx) can be utilized as the amending term to obtain the amended time t' for all the time t detected before the time tx is elapsed, though the amending term is not limited to the rate of change X(tx) at the time tx.

As mentioned above, the amended time t' corresponding to the standard curvature A is obtained based on the rate of change X(tx) and finally, the intraocular pressure of the cornea CO is calculated according to the amended time t' (S6).

Therefore, according to the preferred embodiment described in detail, it can be prevented that the excessive air pressure is directed to the cornea CO of the patient's eye E, thus, discomfort will not be given to the patient, because the rotary solenoid 2 is stopped immediately so that the air pressure does not rise abnormally if it is judged by the microcomputer circuit 6 that the calculated rate of change X(t) exceeds the predetermined value, by monitoring the air pressure continuously.

Further, the time t actually measured can be amended to the optimum time t', thus, the error produced in measuring of the air pressure can be effectively eliminated because the tonometer has the function to amend the erroneous change in the time t due to the delicate change of the air pressure.

Next, another preferred embodiment of the present invention in which the curvature G actually measured closely resembles the standard curvature F, will be described hereinafter.

Generally, the pressure changing curvature versus the time after the rotary solenoid 2 is stopped is represented as a functional equation as two parameters, one is the ratio of both the standard air pressure when the air in the cylinder 1 is started to compress and the measured air pressure (difference in the atmospheric pressure), and the other is the air pressure when the rotary solenoid 2 is stopped. Strictly speaking, such equation represents an approximate expression of the standard curvature F. Therefore, such equation is stored in the memory 7 of the microcomputer circuit 6. At that time, the equation is stored in the form of parameters for defining the equation, and when the air pressure is measured as the actual p-t curvature G in FIG. 3, the curvature G is approximated according to the equation stored in the memory 7, so that the curvature G closely resembles the standard curvature by modifying the parameters. As a result, the curvature G is approximated to the standard p-t curvature F in FIG. 3. Thereafter, the air pressure at the time t is obtained according to the approximated curvature.

Or instead of the above, it is conceivable that a plurality of the pressure changing curvatures are stored in the memory 7 and the most approximate curvature to the measured curvature such as the curvature G in FIG. 3 is selected as the standard curvature such as the curvature F in FIG. 3, for example. Thereafter, the air pressure at the time t is obtained according to the selected curvature.

Here, concerning with selection of stop timing of the rotary solenoid 2, refer to co-pending and commonly assigned U.S. patent application Ser. No. 07/827,610.

Finally, the intraocular pressure of the patient's eye E can be calculated based on both the above approximated or selected curvature and the actually measured time t at which the cornea CO becomes the flat state.

While the invention has been particularly shown and described with reference to preferred embodiments thereof, it will be understood by those skilled in the art that the foregoing and other changes in form and details can be made therein without departing from the spirit and scope of the invention.

What is claimed is:

1. A noncontact type tonometer comprising:
   compressing means for forming compressed air;
   direction means for directing the compressed air to a cornea of a patient's eye;
   deformation detection means for detecting a flat deformation state of the cornea to which the compressed air is directed by the direction means;
   memory means for storing a standard pressure curvature of the compressed air that changes according to passage of time, the standard pressure curvature being inherent in the compressing means;
   pressure detection means for detecting a pressure changing curvature in the compressed air directed by the direction means; and
   processing means for determining an amended pressure changing curvature based on the pressure changing curvature detected by the pressure detection means and the standard pressure curvature stored in the memory means,
   wherein the processing means calculates an intraocular pressure of the patient's eye based on the amended pressure changing curvature.

2. The noncontact type tonometer according to claim 1, wherein the standard pressure curvature is stored in the memory means as an equation.

3. A noncontact type tonometer comprising:
   compressing means for forming compressed air;
   direction means for directing the compressed air to a cornea of a patient's eye;
   deformation detection means for detecting a flat deformation state of the cornea to which the compressed air is directed by the direction means;
   memory means for storing a standard pressure characteristic of the compressed air;
   pressure detection means for detecting a pressure change in the compressed air directed by the direction means; and
   processing means for performing a pressure comparison to compare the pressure change in the compressed air detected by the pressure detection means with the standard pressure characteristic stored in the memory means, and judging whether the pressure change exceeds a predetermined standard based on the result of the pressure comparison,
   wherein the processing means controls the operation of the direction means and stops the drive of the direction means when it is judged that the pressure change exceeds the predetermined standard.

4. The noncontact type tonometer according to claim 3, wherein the memory means stores a plurality types of standard pressure curvatures as the standard pressure characteristic, and the pressure detecting means detects a pressure changing curvature as the pressure change.

5. The noncontact type tonometer according to claim 4, wherein the processing means selects the most approximate curvature to the pressure changing curvature among the standard pressure curvatures stored in the memory means and calculates an intraocular pressure of the patient's eye based on the selected standard pressure curvature.

6. The noncontact type tonometer according to claim 3, further comprising:
   time detection means for detecting the time elapsed until the deformation detection means detects the flat deformation state of the cornea, wherein the processing means determines an amended time based on the time detected by the time detection means when the result of the pressure comparison indicates that the pressure change is different than the standard pressure characteristic and calculates an intraocular pressure of the patient's eye based on the amended time.

7. A noncontact type tonometer comprising:

compressing means for forming compressed air;

direction means for directing the compressed air to a cornea of a patient's eye;

deformation detection means for detecting a flat deformation state of the cornea to which the compressed air is directed by the direction means;

memory means for storing a plurality of types of standard pressure curvatures of the compressed air that change according to passage of time;

pressure detection means for detecting a pressure changing curvature in the compressed air directed by the direction means; and processing means for performing a pressure comparison to compare the pressure changing curvature in the compressed air detected by the pressure detection means with the standard pressure curvatures stored in the memory means and selecting one standard pressure curvature which is the most approximate to the pressure changing curvature, wherein the processing means calculates an intraocular pressure of the patient's eye based on the selected standard pressure curvature.

8. The noncontact type tonometer according to claim 3, wherein the compressing means comprises a cylinder, a piston movably arranged in the cylinder and a solenoid for driving the piston, and further air in the cylinder is compressed by driving the piston through the solenoid.

9. The noncontact type tonometer according to claim 8, wherein the pressure detection means comprises a pressure sensor arranged in the cylinder.

10. The noncontact type tonometer according to claim 7, wherein the compressing means comprises a cylinder, a piston movably arranged in the cylinder and a solenoid for driving the piston, and further air in the cylinder is compressed by driving the piston through the solenoid.

11. The noncontact type tonometer according to claim 10, wherein the pressure detection means comprises a pressure sensor arranged in the cylinder.

* * * * *